United States Patent [19]
Bingel et al.

[11] Patent Number: 5,883,275
[45] Date of Patent: Mar. 16, 1999

[54] PROCESS FOR THE HYDROGENATION OF METALLOCENES

[75] Inventors: Carsten Bingel, Kriftel; Erich Hübscher, Kelkheim; Claus-Peter Niesert, Frankfurt; Roland Zenk, Bad Soden, all of Germany

[73] Assignee: Targor GmbH, Ludwigshafen, Germany

[21] Appl. No.: 961,976

[22] Filed: Oct. 31, 1997

[30] Foreign Application Priority Data

Oct. 31, 1996 [DE] Germany .................. 196 44 040.8

[51] Int. Cl.⁶ .......................... C07F 17/00; C07F 7/00
[52] U.S. Cl. .................... 556/9; 556/11; 556/14; 556/19; 556/21; 556/22; 556/43; 556/53; 556/58; 502/103; 502/117; 526/160; 526/943
[58] Field of Search ............. 556/9, 11, 14, 556/19, 21, 22, 43, 53, 58; 526/943, 160; 502/103, 117

[56] References Cited

U.S. PATENT DOCUMENTS 5,276,208  1/1994  Winter et al. .................. 556/53
5,670,680  9/1997  Newman et al. .............. 556/53

OTHER PUBLICATIONS

Luttikhedde et al., Journal of Organometallic Chemistry, vol. 486, pp. 193–198, 1995.

Primary Examiner—Porfirio Nazario-Gonzalez

[57] ABSTRACT

The present invention relates to a process for the hydrogenation of metallocenes, which comprises treating at least one metallocene containing at least one double bond and/or at least one aromatic substituent in at least one nonhalogenated solvent with hydrogen in the presence of at least one hydrogenation catalyst.

11 Claims, No Drawings

PROCESS FOR THE HYDROGENATION OF METALLOCENES

The present invention relates to a process for preparing hydrogenated and partially hydrogenated metallocenes.

Hydrogenated metallocene such as ethylenebis(tetrahydroindenyl)zirconium dichloride and dimethylsilanediylbis(tetrahydroindenyl)zirconium dichloride are known from J. Am. Chem. Soc. (1996), 118, 2105, J. Mol. Catal. A. Chem. (1995), 102, 59, EP-A-0 643 079, Macromolecules (1994), 27, 4477, Macromolecules (1996), 29, 2331 and JP-A-07 292 019. They are suitable for the preparation of polyolefins such as isotactic polypropylene, copolymers and elastomers. In addition, a series of further hydrogenated metallocenes are known, e.g. EP-A-0 581 754, Organometallics (1993), 12, 4391, JP-A-07 041 521 and Chem. Ber. (1994), 127, 2417. Hydrogenated and partially hydrogenated metallocenes are described as catalyst precursors for the polymerization of olefins, cf. J. Organomet. Chem. (1995), 497, 181, Angew. Chem. (1992), 104, 1373, EP-A-0 344 887, J. Mol. Catal. A: Chem. (1995), 102, 59, EP-A-0 185 918 and EP-A-0 537 686.

The synthesis of hydrogenated or partially hydrogenated metallocenes generally starts from the corresponding metallocenes having aromatic ligands. Thus, hydrogenation of dimethylsilanediylbisindenylzirconium dichloride gives the octahydro derivative dimethylsilanediylbis(4,5,6,7-tetrahydroindenyl)zirconium dichloride. Such and similar reactions have been described many times, cf. JP-A-06 287 224, EP-A-344 887, J. Organomet. Chem. (1995), 497, 181, Organometallics (1991), 10, 1501 and J. Organomet. Chem. (1988), 342, 21.

The known synthetic procedures for hydrogenating the aromatic ligand skeleton of metallocenes in principle all follow the same route. The metallocene is dissolved or suspended in dichloromethane and hydrogenated in the presence of platinum black or platinum dioxide under a high pressure of hydrogen, cf. J. Organomet. Chem. (1988), 342, 21 and EP-A-344 887.

Dichloromethane and other chlorinated solvents can be used in relatively large amounts only if strict safety and environmental regulations are adhered to. In chlorinated solvents, only weakly activating hydrogenation catalysts such as platinum black or platinum dioxide can be used in order to avoid dehalogenation reactions. The dehalogenation reactions lead to decomposition of the product and to corrosion problems.

It is an object of the present invention to provide an economical and environmentally friendly process for the hydrogenation of metallocenes in which high yields are achieved using relatively strongly activating hydrogenation catalysts under mild conditions and low hydrogen pressures.

This object is achieved by a process for the hydrogenation of metallocenes, which comprises treating at least one metallocene containing at least one double bond and/or at least one aromatic substituent (hereinafter: the nonhydrogenated metallocene) in at least one nonhalogenated solvent with hydrogen in the presence of at least one hydrogenation catalyst.

The term nonhydrogenated metallocene refers to the metallocene from which the partially hydrogenated or hydrogenated metallocene is formed by means of the process described in the present invention.

Nonhydrogenated metallocenes such as dimethylsilanediylbisindenylzirconium dichloride or ethylenebisindenylzirconium dichloride are preferably hydrogenated in nonhalogenated aromatic solvents and/or in nonhalogenated oxygen-containing aprotic solvents. Mixtures of the solvents mentioned can also be used.

The product is a metallocene which has an altered structure and altered polymerization properties and differs from the metallocene used in that at least one of the double bonds present in the nonhydrogenated metallocene used is hydrogenated. According to the invention, the nonhydrogenated metallocene is dissolved or suspended in at least one nonhalogenated, preferably aromatic or oxygen-containing aprotic solvent and is hydrogenated with hydrogen in the presence of at least one hydrogenation catalyst.

The starting material can be a pure metallocene (the nonhydrogenated metallocene) or a crude product from a prior metallocene synthesis which contains not only the nonhydrogenated metallocene but also further constituents. The metallocene comprises a transition metal, in particular from group IVb of the Periodic Table of the Elements. The metallocene used can preferably have the following formula:

$$L_mMX_n,$$

where

L are identical or different and are each a π-binded cyclopentadienyl ligand which contains at least one hydrogenable double bond, M is a metal of groups IIIb to VIb of the Periodic Table of the Elements, X is a hydrogen atom, a $C_1$–$C_{40}$-hydrocarbon group such as a $C_1$–$C_{10}$-alkyl, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl group, an OH group, a halogen atom or a pseudohalogen such as nitrile, m is from 1 to 3, n is from 1 to 5 and is equal to the valence of M minus m.

L is preferably vinylcyclopentadienyl, allylcyclopentadienyl, 1,3-bis(4-pentenyl)cyclopentadienyl, indenyl, 2-methylindenyl, 2-methyl-4,5-benzoindenyl, 2-methyl-4-phenylindenyl, 2-methyl-4-(1-naphthyl)indenyl, 1,2,3,4,5,6,7-heptamethylindenyl, 2-methyl-4,6-diisopropylindenyl, 2,4,6-trimethylindenyl, 2-phenylindenyl, fluorenyl or 2,7-di-tert-butylfluorenyl. If a plurality of ligands are present, these can be connected to one another via a bridge.

X is preferably a $C_1$–$C_4$-alkyl, $C_1$–$C_3$-alkoxy, $C_6$–$C_8$-aryl, $C_6$–$C_8$-aryloxy, $C_2$–$C_4$-alkenyl, $C_7$–$C_{12}$-arylalkyl, $C_7$–$C_{12}$-alkylaryl or $C_8$–$C_{12}$-arylalkenyl group, or chlorine.

M is in particular Ti, Zr or Hf.

Examples of nonhydrogenated metallocenes are listed below, but this list does not constitute a limitation:
(cyclopentadienyl)(indenyl)zirconium dichloride,
(methylcyclopentadienyl)(2-methylindenyl)zirconium dichloride,
bisindenylzirconium dichloride,
bisindenylhafnium dichloride,
bis(2-methyl-4,5-benzoindenyl)zirconium dichloride,
bis(2-methylindenyl)zirconium dichloride,
bis(2-methylindenyl)hafnium dichloride,
isopropylidene(cyclopentadienyl)(indenyl)zirconium dichloride,
isopropylidene(cyclopentadienyl)(indenyl)hafnium dibromide,
rac-isopropylidenebisindenylzirconium dichloride, meso-isopropylidenebisindenylzirconium dichloride,
isopropylidene(cyclopentadienyl)(fluorenyl)zirconium dichloride,
diphenylmethylene(cyclopentadienyl)(fluorenyl)zirconium dichloride,
diphenylmethylene(cyclopentadienyl)(fluorenyl)hafnium dichloride,
1-phenylethylidene(cyclopentadienyl)(fluorenyl)zirconium dichloride,
isopropylidene(3-methylcyclopentadienyl)(fluorenyl) zirconium dichloride,
isopropylidene(3-tert-butylcyclopentadienyl)(fluorenyl) zirconium dichloride,
rac-dimethylsilanediylbisindenylzirconium dichloride,
meso-dimethylsilanediylbisindenylzirconium dichloride,
rac-dimethylsilanediylbis(2-methylindenyl)zirconium dibromide,
meso-dimethylsilanediylbis(2-methylindenyl)zirconium dichloride,
rac-dimethylsilanediylbis(2-methyl-4-phenylindenyl) zirconium dichloride,
meso-dimethylsilanediylbis(2-methyl-4-phenylindenyl) zirconium dichloride,
rac-dimethylsilanediylbis[2-methyl-4-(1-naphthyl)indenyl] zirconium difluoride,
rac-dimethylsilanediylbis[2-methyl-4-(1-naphthyl)indenyl] hafnium dichloride,
meso-dimethylsilanediylbis[2-methyl-4-(1-naphthyl) indenyl]zirconium dichloride,
rac-dimethylsilanediylbis(2-methyl-4,5-benzoindenyl) zirconium dichloride,
meso-dimethylsilanediylbis(2-methyl-4,5-benzoindenyl) zirconium dichloride,
rac-dimethylsilanediylbis(4,5-benzoindenyl)zirconium dichloride,
meso-dimethylsilanediylbis(4,5-benzoindenyl)zirconium dichloride,
rac-dimethylsilanediylbis(2-methyl-4,6-diisopropylindenyl) zirconium difluoride,
meso-dimethylsilanediylbis(2-ethylindenyl)zirconium dichloride,
rac-dimethylsilanediylbis(2-ethylindenyl)zirconium dichloride,
meso-dimethylsilanediylbis(2-ethylindenyl)zirconium dichloride,
rac-dimethylsilanediylbis(2-ethyl-4-phenylindenyl) zirconium dichloride,
rac-dimethylsilanediylbis(2-ethyl-4-phenylindenyl)hafnium dichloride,
meso-dimethylsilanediylbis(2-ethyl-4-phenylindenyl) zirconium dichloride,
rac-dimethylsilanediylbis[2-ethyl-4-(1-naphthyl)indenyl] zirconium dichloride,
meso-dimethylsilanediylbis[2-ethyl-4-(1-naphthyl)indenyl] zirconium dichloride,
rac-dimethylsilanediylbis(2-ethyl-4,5-benzoindenyl) zirconium dichloride,
meso-dimethylsilanediylbis(2-ethyl-4,5-benzoindenyl) zirconium dichloride,
rac-dimethylsilanediylbis(4,5-benzoindenyl)zirconium dichloride,
meso-dimethylsilanediylbis(4,5-benzoindenyl)zirconium dichloride,
rac-dimethylsilanediylbis(2-ethyl-4,6-diisopropylindenyl) zirconium dichloride,
meso-dimethylsilanediylbis(2-ethyl-4,6-diisopropylindenyl)zirconium dichloride,
rac-dimethylsilanediylbis(2-ethyl-4,6-dimethylindenyl) zirconium dichloride,
meso-dimethylsilanediylbis(2-ethyl-4,6-dimethylindenyl) zirconium dichloride,
rac-dimethylsilanediylbis(2,4,6-trimethylindenyl)zirconium dichloride,
rac-dimethylsilanediylbis(2,4,6-trimethylindenyl)hafnium dichloride,
meso-dimethylsilanediylbis(2,4,6-trimethylindenyl) zirconium dichloride.

Further constituents can be inorganic salts such as NaCl, LiCl, KCl, KBr, $MgCl_2$, $MgBr_2$, MgBrCl, $CaCl_2$, $AlCl_3$ and also filter aids such as $Na_2SO_4$, quartz flour, Celite. Further constituents can also be organic and organometallic secondary components. Organic secondary components are solvent residues, organic impurities from the starting materials, unreacted starting materials and incompletely reacted intermediates of the metallocene synthesis. Organometallic secondary components can be isomeric metallocenes, oligomeric metallocenes and compounds which have been formed in the preparation of the raw material or had been introduced as a result of impurities in the starting compounds. Organometallic secondary components are all compounds which have at least one metal-carbon bond with the exception of the nonhydrogenated metallocene itself.

Aromatic solvents are solvents which have at least one aromatic six-membered ring per molecule. Examples of nonhalogenated aromatic solvents are benzene, toluene, xylene (as an isomer mixture), o-xylene, m-xylene, p-xylene, mesitylene, tetralin, anisole, cumene 1,2-diethylbenzene, 1,3-diethylbenzene, 1,4-diethylbenzene, 1-ethyl-2-methylbenzene, 1-ethyl-3-methylbenzene, 1-ethyl-4-methylbenzene. Preference is given to anisole, toluene, benzene, xylenes (as a mixture or as pure substance) and tetralin.

Nonhalogenated oxygen-containing aprotic solvents include aromatic and aliphatic ethers such as anisole, ethyl phenyl ether, isopropyl phenyl ether, diethyl ether, di-n-butyl ether, tert-butyl methyl ether, tetrahydrofuran, dioxane. In addition, it is also possible to use esters of aliphatic or aromatic carboxylic acids as solvents, for example ethyl acetate and propyl butyrate.

The process described is carried out in a temperature range from 0° C. to 150° C. In particular, the hydrogenation is carried out at from 15° C. to 100° C.

Suitable hydrogenation catalysts are compounds or elements which do not hydrogenate or only partially hydrogenate the solvent under the hydrogenation conditions employed. Examples of such hydrogenation catalysts are palladium on activated carbon, palladium on barium sulfate, palladium on aluminum oxide, palladium black, palladium sponge, platinum oxide, platinum black, platinum sponge. Preference is given to using palladium catalysts, in particular palladium on activated carbon.

Examples of metallocenes which can be prepared by the process of the invention are listed below, but this list does not constitute a limitation:
(cyclopentadienyl)(4,5,6,7-tetrahydroindenyl)zirconium dichloride,
(methylcyclopentadienyl)(2-methyl-4,5,6,7-tetrahydroindenyl)zirconium dichloride,
bis(2-methyl-4,5-benzo-6,7-dihydroindenyl)zirconium dichloride,
bis(4,5,6,7-tetrahydroindenyl)zirconium dichloride,
bis(2-methyl-4,5,6,7-tetrahydroindenyl)zirconium dichloride,
bis(2-methyl-4,5,6,7-tetrahydroindenyl)hafnium dichloride, isopropylidene(cyclopentadienyl)(4,5,6,7-tetrahydroindenyl)zirconium dichloride,
isopropylidene(cyclopentadienyl)(4,5,6,7-tetrahydroindenyl)hafnium dibromide,
rac-isopropylidenebis(4,5,6,7-tetrahydroindenyl)zirconium dichloride,
meso-isopropylidenebis(4,5,6,7-tetrahydroindenyl)zirconium dichloride,
isopropylidene(cyclopentadienyl)(1,2,3,4,5,6,7,8-octahydrofluorenyl) zirconium dichloride,
diphenylmethylene(cyclopentadienyl)(1,2,3,4,5,6,7,8-octahydrofluorenyl)zirconium dichloride,
diphenylmethylene(cyclopentadienyl)(1,2,3,4,5,6,7,8-octahydrofluorenyl)hafnium dichloride,
1-phenylethylidene(cyclopentadienyl)(1,2,3,4,5,6,7,8-octahydrofluorenyl)zirconium dichloride,
isopropylidene(3-methylcyclopentadienyl)(1,2,3,4,5,6,7,8-octahydrofluorenyl)zirconium dichloride,
isopropylidene(3-tert-butylcyclopentadienyl)(1,2,3,4,5,6,7,8-octahydrofluorenyl)zirconium dichloride,
rac-dimethylsilanediylbis(4,5,6,7-tetrahydroindenyl) zirconium dichloride,
meso-dimethylsilanediylbis(4,5,6,7-tetrahydroindenyl) zirconium dichloride,
rac-dimethylsilanediylbis(2-methyl-4,5,6,7-tetrahydroindenyl)zirconium dichloride,
rac-dimethylsilanediylbis(2-4,5,6,7-tetrahydromethylindenyl)zirconium dibromide,
meso-dimethylsilanediylbis(2-methyl-4,5,6,7-tetrahydroindenyl)zirconium dichloride,
rac-dimethylsilanediylbis(2-methyl-4-phenyl-4,5,6,7-tetrahydroindenyl)zirconium dichloride,
meso-dimethylsilanediylbis(2-methyl-4-phenyl-4,5,6,7-tetrahydroindenyl)zirconium dichloride,
rac-dimethylsilanediylbis[2-methyl-4-(1-naphthyl)-4,5,6,7-tetrahydroindenyl]-zirconium dichloride,
rac-dimethylsilanediylbis[2-methyl-4-(1-naphthyl)-4,5,6,7-tetrahydroindenyl]hafnium dichloride,
meso-dimethylsilanediylbis[2-methyl-4-(1-naphthyl)-4,5,6,7-tetrahydro-indenyl]zirconium dichloride,
rac-dimethylsilanediylbis(2-methyl-4,5,6,7-tetrahydro-4,5-benzoindenyl)zirconium dichloride,
meso-dimethylsilanediylbis(2-methyl-4,5,6,7-tetrahydro-4,5-benzoindenyl)zirconium dichloride,
rac-dimethylsilanediylbis(4,5,6,7-tetrahydro-4,5-benzoindenyl)zirconium dichloride,
meso-dimethylsilanediylbis(4,5,6,7-tetrahydro-4,5-benzoindenyl)zirconium dichloride,
rac-dimethylsilanediylbis(2-methyl-4,6-diisopropyl-indenyl)zirconium dichloride,
rac-dimethylsilanediylbis(2-methyl-4,6-diisopropyl-4,5,6,7-tetrahydroindenyl)-zirconium difluoride,
meso-dimethylsilanediylbis(2-methyl-4,6-diisopropyl-4,5,6,7-tetrahydro-indenyl)zirconium dichloride,
rac-dimethylsilanediylbis(2-ethyl-4,5,6,7-tetrahydroindenyl)zirconium dichloride,
meso-dimethylsilanediylbis(2-ethyl-4,5,6,7-tetrahydroindenyl)zirconium dichloride,
rac-dimethylsilanediylbis(2-ethyl-4-phenyl-4,5,6,7-tetrahydroindenyl)zirconium dichloride,
rac-dimethylsilanediylbis(2-ethyl-4-phenyl-4,5,6,7-tetrahydroindenyl)hafnium dichloride,
meso-dimethylsilanediylbis(2-ethyl-4-phenyl-4,5,6,7-tetrahydroindenyl)zirconium dichloride,
rac-dimethylsilanediylbis[2-ethyl-4-(1-naphthyl)-4,5,6,7-tetrahydroindenyl]-zirconium dichloride,
meso-dimethylsilanediylbis[2-ethyl-4-(1-naphthyl)-4,5,6,7-tetrahydroindenyl]-zirconium dichloride,
rac-dimethylsilanediylbis(2-ethyl-4,5,6,7-tetrahydro-4,5-benzoindenyl)zirconium dichloride,
meso-dimethylsilanediylbis(2-ethyl-4,5,6,7-tetrahydro-4,5-benzoindenyl)zirconium dichloride,
rac-dimethylsilanediylbis(4,5-benzo-4,5,6,7-tetrahydroindenyl)zirconium dichloride,
meso-dimethylsilanediylbis(4,5,6,7-tetrahydro-4,5-benzoindenyl)zirconium dichloride,
rac-dimethylsilanediylbis(2-ethyl-4,6-diisopropyl-4,5,6,7-tetrahydroindenyl)-zirconium dichloride,
meso-dimethylsilanediylbis(2-ethyl-4,6-diisopropyl-4,5,6,7-tetrahydroindenyl)-zirconium dichloride,
rac-dimethylsilanediylbis(2-ethyl-4,6-dimethyl-4,5,6,7-tetrahydroindenyl)zirconium dichloride,
meso-dimethylsilanediylbis(2-ethyl4,6-dimethyl-4,5,6,7-tetrahydroindenyl)-zirconium dichloride,
rac-dimethylsilanediylbis(2,4,6-trimethylindenyl)zirconium dichloride,
rac-dimethylsilanediylbis(2,4,6-trimethyl-4,5,6,7-tetrahydroindenyl)hafnium dichloride,
meso-dimethylsilanediylbis(2,4,6-trimethyl-4,5,6,7-tetrahydroindenyl)zirconium dichloride.

Surprisingly, the novel process has many advantages. The use of nonhalogenated (e.g. nonchlorinated) solvents makes it possible to employ more active hydrogenation catalysts and the reactions can be carried out at relatively low hydrogen pressures. This is of particular interest for industrial applications. The chlorinated solvents which are dubious from safety and environmental points of view are avoided. The use of nonhalogenated aromatic hydrocarbons or nonhalogenated slightly polar aprotic solvents such as ether makes the subsequent work-up of the metallocenes easier. In the case of the preferred solvents such as anisole, toluene, benzene, xylene, tert-butyl methyl ether and tetrahydrofuran, the product can be completely dissolved at elevated temperature, the hydrogenation catalyst can be separated off and the product can be crystallized. In this work-up, a wider temperature range at temperatures above 0° C. is available when compared to dichloromethane. Dichloromethane has hitherto been used exclusively in the prior art. Low temperatures (below 0° C.) can thus be avoided in the crystallization. The good solubility of the hydrogenated products in nonhalogenated aromatic solvents at elevated temperature makes possible the hydrogenation of very concentrated metallocene suspensions, which is advantageous in terms of a good space-time yield. In addition, compared to known processes, the required amounts of hydrogenation catalyst are significantly cheaper. If metallocenes are extracted from their crude product mixtures using aromatic or aprotic aliphatic solvents, it may be possible to subject such extracts as solution or suspension to a subsequent hydrogenation directly and without a change of solvent.

The present invention is illustrated by the following examples.

EXAMPLES

Example 1

5.0 g (12.0 mmol) of rac-ethylenebis(indenyl)zirconium dichloride and 0.3 g (0.28 mmol) of palladium (10% on activated carbon) were suspended in 100 ml of toluene and hydrogenated at 70° C. and a hydrogen pressure of 20 bar. After 5 hours, the reaction mixture was filtered hot, evaporated to half its volume and crystallized at 0°–5° C. Yield: 4.6 g (10.8 mmol; 90%) rac-ethylenebis(4,5,6,7-tetrahydroindenyl)zironium dichloride.

Example 2

5.0 g (12.0 mmol) of rac-ethylenebis(indenyl)zirconium dichloride and 0.3 g (0.28 mmol) of palladium (10% on activated carbon) were suspended in 100 ml of anisole and hydrogenated at 70° C. and a hydrogen pressure of 20 bar. After 6 hours, the reaction mixture was filtered hot, evaporated to half its volume and crystallized at 0°–5° C. Yield: 4.3 g (10.0 mmol; 84%) rac-ethylenebis(4,5,6,7-tetrahydroindenyl)zironium dichloride.

Comparative Example 1

5.0 g (12.0 mmol) of rac-ethylenebis(indenyl)zirconium dichloride and 0.3 g (1.3 mmol) of $PtO_2$ were suspended in 100 ml of dichloromethane and hydrogenated at 25° C. and a hydrogen pressure of 100 bar. After 5 hours, the reaction mixture was diluted with 2500 ml of dichloromethane, filtered, freed of solvent under reduced pressure and the residue was recrystallized from hot toluene. Yield: 3.0 9 (6.9 mmol; 58%) of rac-ethylenebis(4,5,6,7-tetrahydroindenyl)zirconium dichloride.

Comparative Example 2
as described in J. Organomet. Chem. (1985), 288, 63

1 g (2.4 mmol) of rac-ethylenebis(indenyl)zirconium dichloride and 75 mg (0.33 mmol) of $PtO_2$ were suspended in 25 ml of dichloromethane and hydrogenated (room temperature) for 30 minutes under 100 bar of hydrogen in a 100 ml laboratory autoclave. The mixture was diluted with 500 ml of dichloromethane, filtered and the filtrate was evaporated. The pale brown solid residue was thoroughly washed with petroleum ether and recrystallized from hot toluene. Yield: 650 mg (1.5 mmol; 65%) of rac-ethylenebis(4,5,6,7-tetrahydroindenyl)zirconium dichloride.

Comparative Example 3
as described in J. Organomet. Chem. (1988), 342, 21

4.2 g (10.0 mmol) of rac-ethylenebis(indenyl)zirconium dichloride and 100 mg $PtO_2$ (0.44 mmol) were suspended in 70 ml of dichloromethane and hydrogenated (room temperature) for 8 hours under 70 bar of hydrogen. The mixture was diluted with 300 ml of dichloromethane, filtered through Celite and the filtrate was evaporated under reduced pressure. The residue was recrystallized from hot toluene. Yield: 2.7 g (6.5 mmol; 65%) of rac-ethylenebis(4,5,6,7-tetrahydroindenyl)zirconium dichloride.

Example 3

5.0 g (11.2 mmol) of rac-dimethylsilanediylbis(indenyl)zirconium dichloride and 0.3 g (0.28 mmol) of palladium (10% on activated carbon) were suspended in 100 ml of toluene and hydrogenated at 70° C. under a hydrogen pressure of 20 bar. After 5 hours, the reaction mixture was filtered hot, evaporated to half its volume and crystallized at 0°–5° C. Yield: 4.7 g (10.4 mmol; 93%) of rac-dimethylsilanediylbis(4,5,6,7-tetrahydroindenyl)zirconium dichloride.

Example 4

5.0 g (11.2 mmol) of rac-dimethylsilanediylbis(indenyl)zirconium dichloride and 0.3 9 (0.28 mmol) of palladium (10% on activated carbon) were suspended in 100 ml of anisole and hydrogenated at 70° C. under a hydrogen pressure of 20 bar. After 6 hours, the reaction mixture was filtered hot, evaporated to half its volume and crystallized at 0°–5° C. Yield: 4.5 g (9.9 mmol; 88%) of rac-dimethylsilanediylbis(4,5,6,7-tetrahydroindenyl)zirconiun dichloride.

Comparative Example 4

5.0 g (11.2 mmol) of rac-dimethylsilanediylbis(indenyl)zirconium dichloride and 0.3 g (1.0 mmol) of $PtO_2$ (hydrate) were suspended in 100 ml of dichloromethane and hydrogenated at room temperature under a hydrogen pressure of 20 bar. After 5 hours, the reaction mixed was filtered, freed of solvent under reduced pressure and the residue was recrystallized from hot toluene. Yield: 1.8 g (3.9 mmol; 35%) of rac-dimethylsilanediylbis(4,5,6,7-tetrahydroindenyl)zirconium dichloride.

Comparative Example 5
as described in J. Organomet. Chem. (1995), 497, 181

6.33 g (14.1 mmol) of rac-dimethylsilanediylbis(indenyl)zirconium dichloride and two spatula tips of $PtO_2$ (hydrate) were suspended in 500 ml of dichloromethane and hydrogenated for three hours at room temperature under a hydrogen pressure of 17 bar in a steel autoclave. The resulting solution was filtered through a D4 frit, evaporated to dryness and recrystallized from toluene at 70° C. Yield: 2.06 g (4.5 mmol; 32%) of rac-dimethylsilanediylbis(4,5,6,7-tetrahydroindenyl)zirconium dichloride.

Comparative Example 6
as described in EP-A-0 344 887

A not precisely defined amount of rac-dimethylsilanediylbis(indenyl)zirconium dichloride and 0.5 g (2.6 mmol) of platinum black or (2.2 mmol) of $PtO_2$ were suspended in 200 ml of dichloromethane and hydrogenated for four hours at 45° C. under a hydrogen pressure of 41 bar in a steel autoclave. The resulting solution was filtered and evaporated to less than 100 ml. rac-Dimethylsilanediylbis(4,5,6,7-tetrahydroindenyl)zirconium dichloride crystallized from the solution (maximum yield: 20 g (44 mmol) based on 44 ml (380 mmol) of indene; 23%).

Example 5

4.0 g (9.0 mmol) of rac-dimethylsilanediylbis(2-methyl-4,5-benzindenyl)zirconium dichloride and 0.3 9 (0.28 mmol) of palladium (10% on activated carbon) were suspended in 100 ml of toluene and hydrogenated at 70° C. under a hydrogen pressure of 30 bar. After 6 hours, the reaction mixture was filtered hot, extracted with 2000 ml of hot toluene and evaporated to 300 ml. The partially hydrogenated product rac-dimethylsilanediylbis (2-methyl-6,7-dihydro-4,5-benzindenyl)zirconium dichloride crystallized out at 0°–5° C. Yield: 2.6 g (4.5 mmol; 50%). $^1$H-NMR (300 MHz, $CDCl_3$): d=7.42 (m, 2H); 7.3–7.14 (m, 4H); 7.2 (m, 2H); 6.96 (s, 2H); 2.82 (m, 4H); 2.25 (s, 6H); 1.02 (s, 6H).

Example 6

3.0 g (6.9 mmol) of rac-isopropylidenebis(indenyl)zirconium dichloride and 0.3 g (0.28 mmol) of palladium (10% on activated carbon) were suspended in 100 ml of toluene and hydrogenated at 50° C. under a hydrogen pressure of 60 bar. After 6 hours, the reaction mixture was filtered hot, extracted with 200 ml of hot toluene and evaporated to 40 ml. The product crystallized out at 0°–5° C. Yield: 1.9 g (4.3 mmol; 63%) of rac-isopropylidenebis(4,5,6,7-tetrahydroindenyl)zirconium dichloride. $^1$H-NMR (300 MHz, $CDCl_3$): d=6.37 (d, 2H); 5.48 (d, 2H); 2.6–3.0 (m, 6H); 2.3–2.5 (m, 2H); 1.4–2.0 (m, 8H); 1.85 (s, 6H).

Example 7

3.0 g (7,8 mmol) of isopropylidene(cyclopentadienyl)(indenyl)zirconium dichloride and 0.3 9 (0.28 mmol) of palladium (10% on activated carbon) were suspended in 100 ml of toluene and hydrogenated at 50° C. under a hydrogen pressure of 20 bar. After 6 hours, the reaction mixture was filtered hot and evaporated to 40 ml. The product crystallized out at 0°–5° C. Yield: 2.1 g (5.4 mmol; 69%) of isopropylidene (cyclopentadienyl)(4,5,6,7-tetrahydroindenyl)zirconium dichloride. $^1$H-NMR (300 MHz, CDCl$_3$): d=6.78 (m, 1H); 6.62 (m, 1H); 6.25 (m, 1H); 5.72 (m, 1H); 5.62 (m, 2H); 2.9–2.6 (m, 3H); 2.5–2.3 (m, 1H); 2.0–1.3 (m, 4H); 1.90 (s, 3H); 1.80 (s, 3H).

We claim:

1. A process for the hydrogenation of metallocenes, which comprises treating at least one metallocene containing at least one double bond and/or at least one aromatic substituent in at least one nonhalogenated solvent with hydrogen in the presence of at least one hydrogenation catalyst.

2. The process as claimed in claim 1, wherein the metallocene comprises a transition metal compound of group IVb of the Periodic Table of the Elements.

3. The process as claimed in claim 1, wherein at least one metallocene is hydrogenated in nonhalogenated aromatic solvents and/or in nonhalogenated oxygen-containing aprotic solvents.

4. The process as claimed in claim 1, wherein the nonhalogenated aromatic solvents used are benzene, toluene, xylene, o-xylene, m-xylene, p-xylene, mesitylene, tetralin, anisole, cumene, 1,2-diethylbenzene, 1,3-diethylbenzene, 1,4-diethylbenzene, 1-ethyl-2-methylbenzene, 1-ethyl-3-methylbenzene, or 1-ethyl-4-methylbenzene.

5. The process as claimed in claim 1, wherein the nonhalogenated oxygen-containing aprotic solvents used are ethers ether, or esters or aliphatic or aromatic carboxylic acids.

6. The process as claimed in claim 1, wherein the temperature is set in the range from 0° to 150° C.

7. The process as claimed in claim 1, wherein the hydrogenation catalysts used are palladium catalysts.

8. The process as claimed in claim 1, wherein the nonhalogenated aromatic solvent used is anisole, toluene, benzene, xylene or tetralin.

9. The process as claimed in claim 5, wherein the nonhalogenated oxygen-containing aprotic solvents used are anisole, ethyl phenyl ether, isopropyl phenyl ether, diethyl ether, di-n-butyl ether, tert-butyl methyl ether, tetrahydrofuran, dioxane, ethyl acetate and propyl butyrate.

10. The process as claimed in claim 6, wherein the temperature is from 15° C. to 150° C.

11. The process as claimed in claim 7, wherein the hydrogenation catalyst used is palladium on activated carbon, palladium on barium sulfate, palladium on aluminum oxide, palladium black, palladium sponge, platinum oxide, platinum black or platinum sponge.

* * * * *